United States Patent
Kofler et al.

(10) Patent No.: US 10,369,522 B2
(45) Date of Patent: Aug. 6, 2019

(54) ELECTROCHEMICAL CELL

(71) Applicants: UNIVERSITÄT INNSBRUCK, Innsbruck (AT); MEDIZINISCHE UNIVERSITÄT INNSBRUCK, Innsbruck (AT)

(72) Inventors: Markus Kofler, Innsbruck (AT); Julia Dumpfarth, Innsbruck (AT); Michael Grimm, Vienna (AT); Georg Grimm, Pörtschach (AT); Gulnara Fauland, Dornbirn (AT); Thomas Bechtold, Dornbirn (AT)

(73) Assignees: UNIVERSITAT INNSBRUCK, Innsbruck (AT); MEDIZINISCHE UNIVERSITAT INNSBRUCK, Innsbruck (AT)

( * ) Notice: Subject to any disclaimer, the term of this patent is extended or adjusted under 35 U.S.C. 154(b) by 401 days.

(21) Appl. No.: 15/107,663

(22) PCT Filed: Dec. 23, 2014

(86) PCT No.: PCT/EP2014/079244
§ 371 (c)(1),
(2) Date: Jun. 23, 2016

(87) PCT Pub. No.: WO2015/097248
PCT Pub. Date: Jul. 2, 2015

(65) Prior Publication Data
US 2016/0325230 A1   Nov. 10, 2016

(30) Foreign Application Priority Data

Dec. 23, 2013 (EP) .................................... 13199304

(51) Int. Cl.
*B01D 61/46* (2006.01)
*B01D 61/42* (2006.01)
(Continued)

(52) U.S. Cl.
CPC ......... *B01D 61/427* (2013.01); *B01D 61/422* (2013.01); *B01D 61/46* (2013.01);
(Continued)

(58) Field of Classification Search
None
See application file for complete search history.

(56) References Cited

U.S. PATENT DOCUMENTS

| 3,440,159 A | 4/1969 | McRae et al. |
| 3,677,923 A * | 7/1972 | Bier ...................... B01D 61/56 |
| | | 204/543 |

(Continued)

FOREIGN PATENT DOCUMENTS

| EP | 0095170 | 11/1983 |
| EP | 1568705 | 8/2005 |
| WO | WO0071999 | 11/2000 |

OTHER PUBLICATIONS

Comper et al., "Model connective tissue systems: Measurement of ion flux across gel membranes containing proteoglycan", Journal of Colloid and Interface Science, Academic Press, New York, vol. 3, No. 3, Dec. 1975, pp. 379-390.

*Primary Examiner* — Louis J Rufo
*Assistant Examiner* — Salil Jain
(74) *Attorney, Agent, or Firm* — Workman Nydegger

(57) ABSTRACT

Electrochemical cell array for the treatment of a sample via electro-(end-)osmotic flow, comprising
(i) an electrode chamber, comprising a cathodic compartment (CC) and an anodic compartment (AC),
(ii) a cathode (C), being arranged in the cathodic compartment (CC),
(iii) an anode (A), being arranged in the anodic compartment (AC),
(iv) an intermediate cathodic compartment (C1)
(v) an intermediate anodic compartment (A1)
(Continued)

Figure 1:
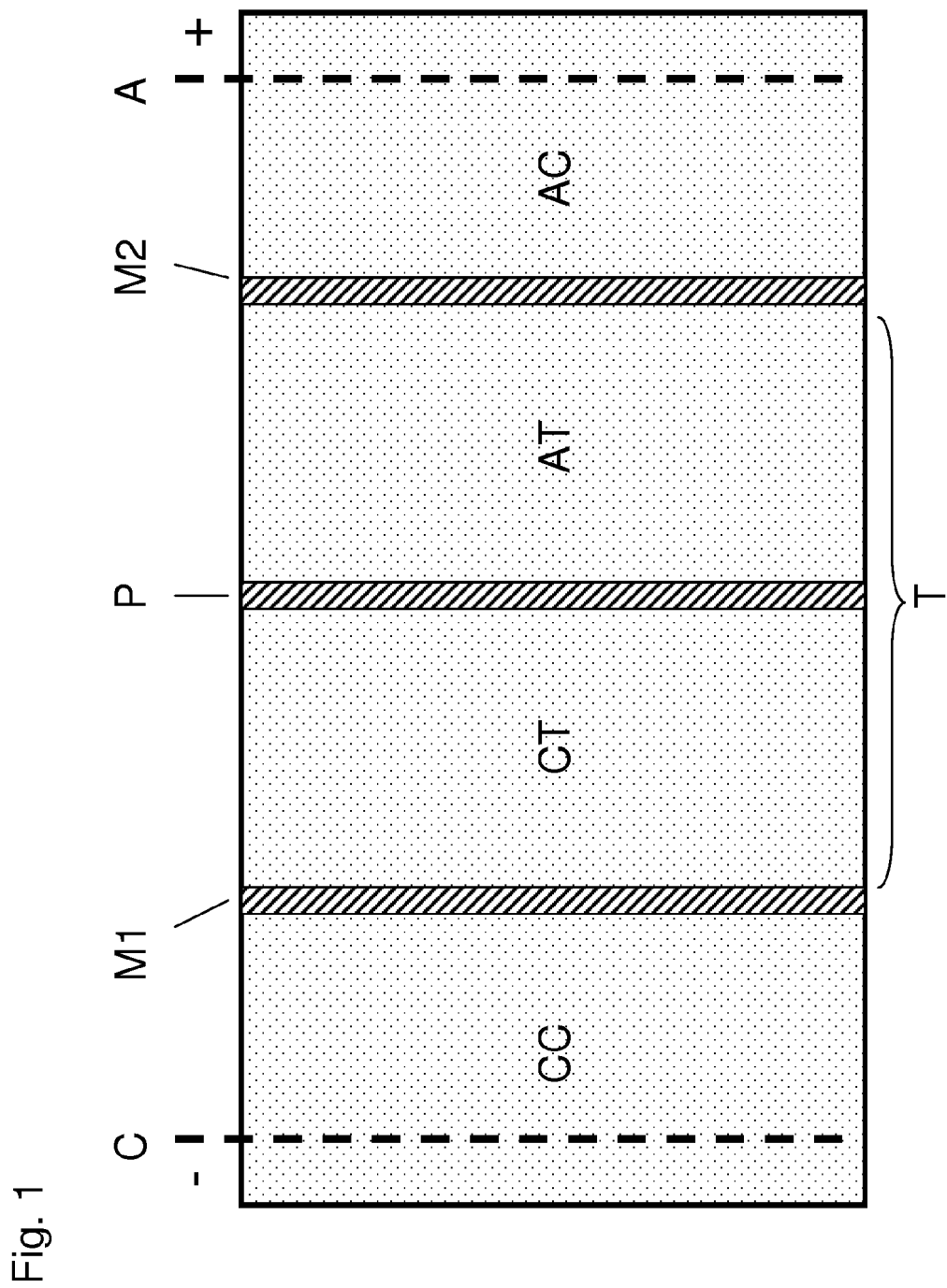

(iv) a first selective membrane (M1) being arranged between said cathodic compartment (CC) and said first intermediate cathodic compartment (C1)
(v) a second selective membrane (M2) being arranged between said anodic compartment (AC) and said first intermediate anodic compartment (A1)
(vi) a treatment compartment (T) for the sample being arranged between said intermediate cathodic compartment (C1) and said intermediate anodic compartment (A1), further comprising a first separator membrane (S1) between said treatment compartment (T) and said intermediate cathodic compartment (C1) and a second separator membrane (S2) arranged between said treatment compartment (T) and said intermediate anodic compartment (A1).

13 Claims, 3 Drawing Sheets

(51) Int. Cl.
*G01N 27/28* (2006.01)
*G01N 27/403* (2006.01)

(52) U.S. Cl.
CPC .... *B01D 2313/30* (2013.01); *B01D 2313/345* (2013.01); *B01D 2325/42* (2013.01); *G01N 27/283* (2013.01); *G01N 27/403* (2013.01)

(56) References Cited

U.S. PATENT DOCUMENTS

| | | | |
|---|---|---|---|
| 5,087,338 A | * | 2/1992 | Perry ............... B01D 57/02 204/541 |
| 2014/0288398 A1 | * | 9/2014 | Simberg ............ C12Q 1/6806 600/309 |

* cited by examiner

ELECTROCHEMICAL CELL

The present invention relates to electrochemical cells for the treatment of samples, in particular solid or liquid biological material, via electro-(end-)osmotic flow, the electrochemical cell comprising an electrode chamber with a cathodic compartment and an anodic compartment, a cathode, being arranged in said cathodic compartment and an anode, being arranged in said anodic compartment. The invention further relates to the use of such an electrochemical cell.

By applying an external electric field to a liquid or solid biological material that comprises mobile ions in an electrochemical cell, different phenomena are observed depending on the conditions, surroundings and the chemical environment in the electrochemical cell. These phenomena include electrolysis, electrodialysis, electrophoresis, and electro-osmosis (also referred to as electro-endosmosis).

Literature before the 1950s did not distinguish between these phenomena. However, due to a good understanding of the underlying chemical and physical processes it is now possible to draw a line between these phenomena. In contrast to electrolysis, where a chemical reaction takes place, electrodialysis, electrophoresis and electro-(end-)osmosis involve transport processes in the electrolyte which are caused by the electric current.

Electrolysis:

During electrolysis a chemical reaction/decomposition of a substance takes place by the action of an electric current. The process is limited to the surface of the electrodes and proceeds according to Faraday's law, which governs the relationship between flow and chemical reaction. The composition of the electrolyte changes during electrolysis through the electrode reaction. In addition a certain minimum conductivity of the electrolyte is required. However, processes occurring in the electrolyte itself are not included in the definition of electrolysis.

In the phenomena described below in more detail an electrochemical conversion is required due to electrolysis at the electrodes in order to initiate the transport processes and to maintain a current flow. However, these processes are only provided for the occurrence of phenomena but not directly part of the underlying principles. The chemical processes occurring at the electrodes can therefore be separated from the other transport phenomena by appropriate barriers.

Electro-Dialysis:

In electro-dialysis ions are transported from one solution through ion-exchange membranes to another solution by applying an electric potential difference. There is a selective flow of cations to the cathode and anions to the anode. If the electrodes are separated by a so-called ion-selective membrane, ions migrate according to their rate of migration to the corresponding electrodes. If the membrane is not ion selective, anions and cations are not separated in the electrolyte.

In aqueous solution ions comprise a hydration shell and by movement of an ion approximately 4 to 6 water molecules are coupled to the flow of said ion. The flow of charge of one Faraday (96485 As/mol) corresponds to a transport volume of 70 to 110 ml of water.

Electrophoresis:

In electrophoresis, charged colloidal substances are separated. The process principle takes advantage of the different migration velocities of charged carriers (dispersed particles with surface charges) in the electric field in the electrolyte (cataphoresis). Since electrophoresis is used for separating high-molecular materials a strong electric field has to be applied and the separation takes place in a carrier medium. Such a carrier medium is also necessary in order to avoid back-mixing of slowly migrating colloidal/high molecular weight substances.

Electro-(End-)Osmosis:

The principle of electro-osmosis (or electro-endosmosis) is based on the presence of a porous material that comprises charged carriers that are bound or adsorbed on the inside of the pores. In an external electric field (e.g. caused by a remote electrolysis process) a charge flow occurs through the porous three-dimensional system. Since some of the charges are localized (e.g. the negative charges) only ions with opposite charge (e.g. cations) migrate in the porous system. The liquid in the pore starts moving due to the ion movement. An ion and fluid migration is observed in the direction of the distant cathode. In electro-osmosis the negative charged carriers are localised and a flow of cations to the cathode is observed, in electro-endomosis the positive charged carriers are localized and a flow of anions to the anode is observed, since the anions are mobile. Within the meaning of the present invention the term electro-(end-)osmosis refers to both electro-osmosis and electro-endosmosis.

U.S. Pat. No. 3,440,159 describes a method for the electro-osmotic separation of non-charged molecules from a solution that also comprises high molecular compounds. An electrochemical cell array with two different ion-exchange membranes is used. The separating membranes are ion-selective-membranes and exhibit different porosities. The substances that are to be separated are non-charged low-molecular weight substances, in particular carbohydrates that are transported into a compartment with the electro-osmotic flow. The method according to U.S. Pat. No. 3,440,159 enables separation of solutions of carbohydrates and high-molecular weight substances. The separating media are ion-exchange membranes, which may exhibit the same polarity but they have to show a different permeability. An ion-selective membrane should be permeable for low molecular weight substances, the other membrane is impermeable. By means of an ion-selective-membrane with different permeability the desired decrease and increase of substances via electro-osmosis is possible.

The electro-osmotic principle can be applied for different separation methods. One disadvantage of known electrochemical devices that apply the electro-(end-)osmotic principle is that the due to the electric field that has to be applied, a migration of ions occurs causing the electro-(end-)osmotic flow, which in succession causes a concentration shift in the treatment solution. In the treatment of biological material, however, it is vital to maintain the ion concentrations and the pH constant in the solution since any changes might reduce or destroy the biological activity of the biological material.

Hence, it is an object of the present invention to provide an electrochemical cell, wherein this problem is overcome. In particular the electrochemical cell should enable the treatment of biological material without negatively influencing the activity of the biological material.

This problem is solved by an electrochemical cell according to claim 1.

The electrochemical cell for the treatment of a sample via electro-osmotic flow, comprises
 (i) an electrode chamber, comprising a cathodic compartment and an anodic compartment,
 (ii) a cathode, being arranged in the cathodic compartment,
 (iii) an anode, being arranged in the anodic compartment,
 (iv) an intermediate cathodic compartment, (v) an intermediate anodic compartment,
(iv) a first selective membrane being arranged between said cathodic compartment and said first intermediate cathodic compartment,
(v) a second selective membrane being arranged between said anodic compartment and said first intermediate anodic compartment,
(vi) a treatment compartment for the sample being arranged between said intermediate cathodic compartment and said intermediate anodic compartment, further comprising a first separator membrane between said treatment compartment and said intermediate cathodic compartment and a second separator membrane arranged between said treatment compartment and said intermediate anodic compartment.

In a preferred embodiment the sample is biological material.

The electrochemical cell as defined above is most suitable for liquid biological material by simply placing it into the treatment compartment. This electrochemical cell may also be used for treating solid biological material, but in this case the electro-(end-)osmotic treatment takes longer.

In one embodiment of the invention especially suited for solid samples the electrochemical cell further comprises
(vii) a holding device for solid or essentially solid samples, in particular solid biological material, placed in said treatment compartment dividing the treatment compartment into an cathodic treatment compartment and an anodic treatment compartment. This embodiment is particularly suitable for the treatment of solid biological material since it is faster than the above mentioned electrochemical cell with only five compartments. In this embodiment the cathodic treatment compartment is adjacent to the first separator membrane and the anodic treatment compartment is adjacent to the second separator membrane. The holding device is so configured that when it carries a solid sample and is placed in the treatment compartment said holding device divides the treatment compartment into two separated compartments, a cathodic treatment compartment and an anodic treatment compartment, with the solid sample being exposed to both the cathodic treatment compartment and the anodic treatment compartment. The holding device is placed between cathodic treatment compartment and anodic treatment compartment so migration within the electrochemical cell has to occur through biological material placed in the holding device.

The term "treatment of a sample" includes any process that makes use of an electro-(end-)osmotic effect with the sample. In particular it includes purification of the sample (such as biological material) in order to remove undesired compounds and ions as well as transporting desired compounds to and/or into the sample such as biological material. The term solid sample or solid biological material refers to any sample with a three-dimensional-shape such as tissue, membranes, bones, etc., whereas the term liquid sample or liquid biological material refers to samples that have no structure and behave like a liquid such as blood, plasma, cerebrospinal fluid, etc.

The electrodes may be made of conventional electrode materials. In a preferred embodiment, the electrodes comprise graphite, platinum or other chemically-resistant electrode material. In a particularly preferred embodiment the electrodes comprise noble metal oxide coated titanium.

In one embodiment of the invention the first separator membrane and the second separator membrane are composed of essentially the same material. This means that the first separator membrane and the second separator membrane are made of the material with the same or almost the same chemical and physical structure and properties.

In a preferred embodiment the first separator membrane and the second separator membrane are electro-(end-)osmotically active membranes. An electro-(end-)osmotically active membrane is a porous membrane wherein the pores contain localized charges at the surface. Localized charges may e.g. arise from surface ions (such as deprotonated acids, e.g. deprotonated carboxylic acids) or dipoles forming van der Waal's forces or combinations thereof.

The first separator membrane and the second separator membrane might be a gel. The gel might be a known gel from electrophoresis. Such a gel is preferably selected from the group consisting of agarose gel, pectin gel, starch or swollen cellulose.

The first selective membrane and the second selective membrane might be selected from the group consisting of semi-permeable membrane, ion-exchange-membrane, ion-exchange-diaphragm or a combination thereof.

In a further embodiment the electrochemical cell may comprise at least one additional compartment. In particular such an additional compartment may be one or more additional intermediate (anodic and/or cathodic) compartments. In a preferred embodiment the electrochemical cell comprises 2*n additional compartments (pairs of compartments) with n being a natural number. For instance, such an additional pair of compartments could comprise a second intermediate cathodic compartment and a second intermediate anodic compartment, the second intermediate cathodic compartment being arranged between (first) intermediate cathodic compartment and treatment chamber, the second intermediate anodic compartment being arranged between (first) intermediate anodic compartment and treatment chamber, with an additional pair of membranes. Such an additional pair of compartments may in addition or as alternative also be a pre-cathodic chamber and a pre-anodic chamber being arranged prior to the cathodic chamber and prior to the anodic chamber, respectively.

In one embodiment the first separator membrane and the second separator membrane comprise a biological material that is essentially the same material as the biological material to be treated. E.g. if the biological material to be treated is pericardium then the first and second separator membrane may comprise pericardium. This further reduces changes in the electrolyte environment. The biological material embedded in the first and second separator membrane might e.g. be embedded in a gel such as agarose.

During treatment the biological material is fixed or placed in the electrochemical cell so that under the influence of an electrical field the current flow has to migrate through the biological material to be treated thereby producing a strong electro-osmotic flow.

The sample to be treated has to be accessible for electro-(end-)osmotic treatment. Biological material normally is accessible for electro-(end-)osmotic treatment without preparation; for some solid biological material it might be useful if it is presented as a film.

In a preferred embodiment, certain solutes or ions are selectively removed from the biological material to be treated and, if necessary, replaced by other solutes or ions.

A preferred use of present invention is the electro-(end-)osmotic treatment of solid and liquid biological material, as for example pericardium fixed with glutardialdehyde or body fluids. Due to the electro-(end-)osmotic flow, a strong mass transfer within the solid and liquid biological material can be achieved. It is for instance possible to transport reactive chemicals such as amino acids into the biological material or to remove compounds that adversely affect the biological material itself or the further use of the biological material.

In liquid biological material e.g. low molecular weight components such as glucose, urea, creatinine, salts can be removed.

The above mentioned problem is of course also solved by a method of treating a sample—in particular biological material—via electro-(end-)osmotic flow using an electrochemical cell as described above, by placing an electrolyte in the compartments, the sample in the treatment compartment, and applying an electric current to the electrodes.

Basically, the invention is based on the finding that by using at least the above mentioned five compartments, the ionic strength and pH in the vicinity of the sample does not change substantially thus the sample is not negatively influenced due to a change in the near environment of the sample even though there is an electro-osmotic flow through the sample.

As mentioned above an electrochemical cell comprising five compartments is most suitable for liquid samples. The method for treating solid samples via electro-osmotic flow using an electrochemical cell comprising six compartments is most useful for solid samples.

In a preferred embodiment the sample is biological material, more preferably pericardium.

In a preferred embodiment a low-frequency alternating current is applied to the electrochemical cell.

In another embodiment, ion-containing aqueous solutions are used as electrolyte. Preferred ions are selected from the class of alkali and alkaline earth metal salts. In a particularly preferred embodiment, soluble alkali metal phosphates are used as the buffer system.

While the pH-value of the anodic compartment and cathodic compartment, respectively may be selected in a wide range, the pH-value of the electrolyte in the intermediate cathodic compartment, intermediate anodic compartment, treatment compartment, the cathodic treatment compartment if present and the anodic treatment compartment if present preferably lies in the range between 3 and 10, in a particularly preferred embodiment, the pH range corresponds to the optimum for the sample (such as biological material) that is to be treated. Adjustment may e.g. be done by a potassium phosphate buffer.

In a preferred embodiment the concentration of dissolved salts in the electrolyte is between 0.1 mM and 1 M. In a particularly preferred embodiment, the electrolyte comprises between 5 and 50 mM phosphate buffer. An alkali can be used as supporting electrolyte.

The current density to be used depends on the cross sectional area of the biological material but can vary within a wide range. Preferred current densities are between 0.1 mA/cm$^2$ and 1 A/cm$^2$. In a particularly preferred embodiment the current density is between 1 mA/cm$^2$ and 100 mA/cm$^2$. The upper region of the current density depends on the conductivity of the material to be treated. The lower value for the current density is defined by the needed treatment time, because the electro-(end-) osmotic flow decreases with decreasing current density which can lead to a prolongation of the treatment time.

The invention further relates to the use of an electrochemical cell as mentioned above for treating solid biological material. In this case the biological material most preferably is pericardium.

The invention further relates to the use of an electrochemical cell as mentioned above for treating liquid biological material. The biological material may for instance be selected from the group consisting of blood or plasma.

The invention is further illustrated by the attached figures and their description as well as a set of examples.

FIG. 1 schematically shows an electrochemical cell array according to the prior art.

Figure 2:
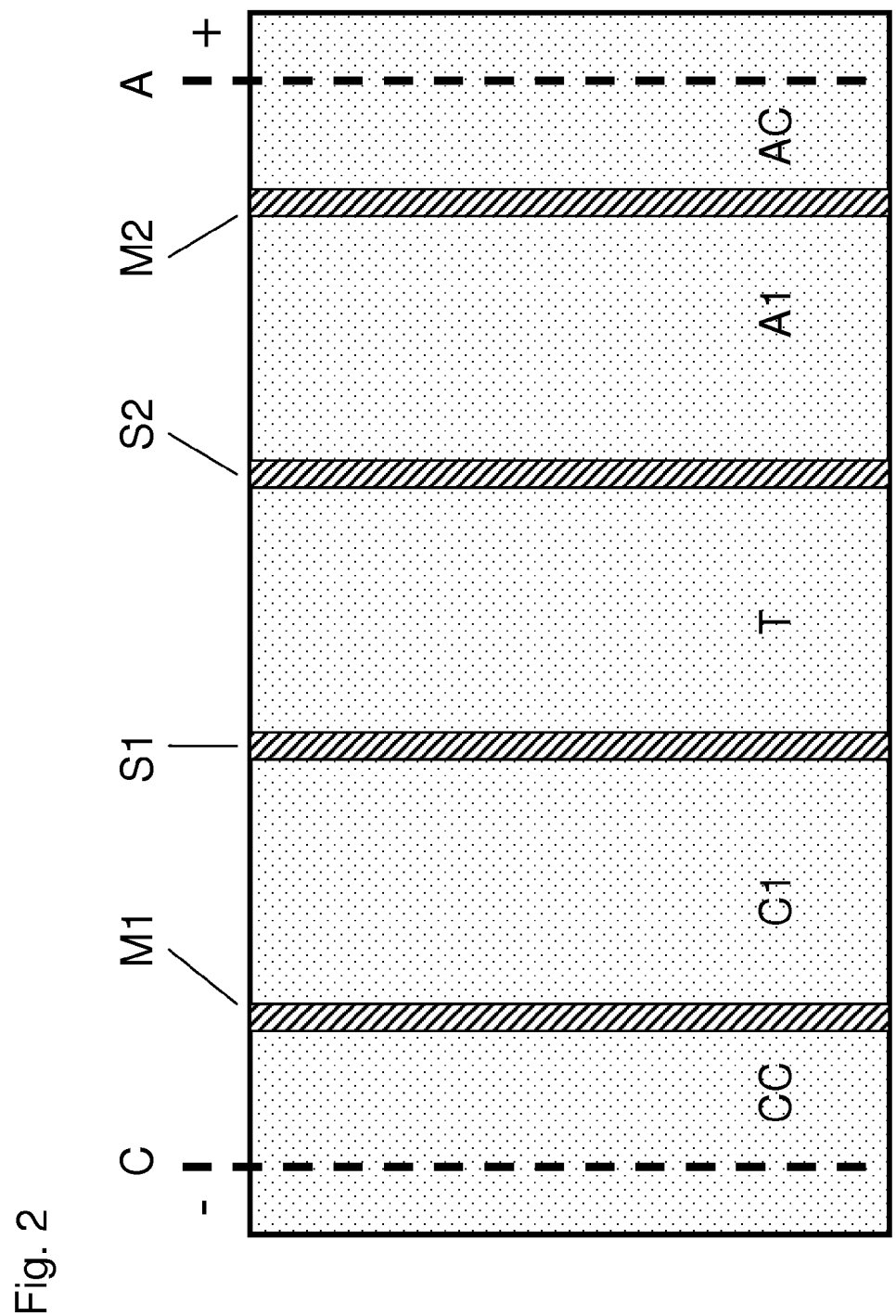

FIG. 2 schematically shows an electrochemical cell array for the treatment of samples via electro-(end-)osmotic flow with five compartments.

Figure 3:
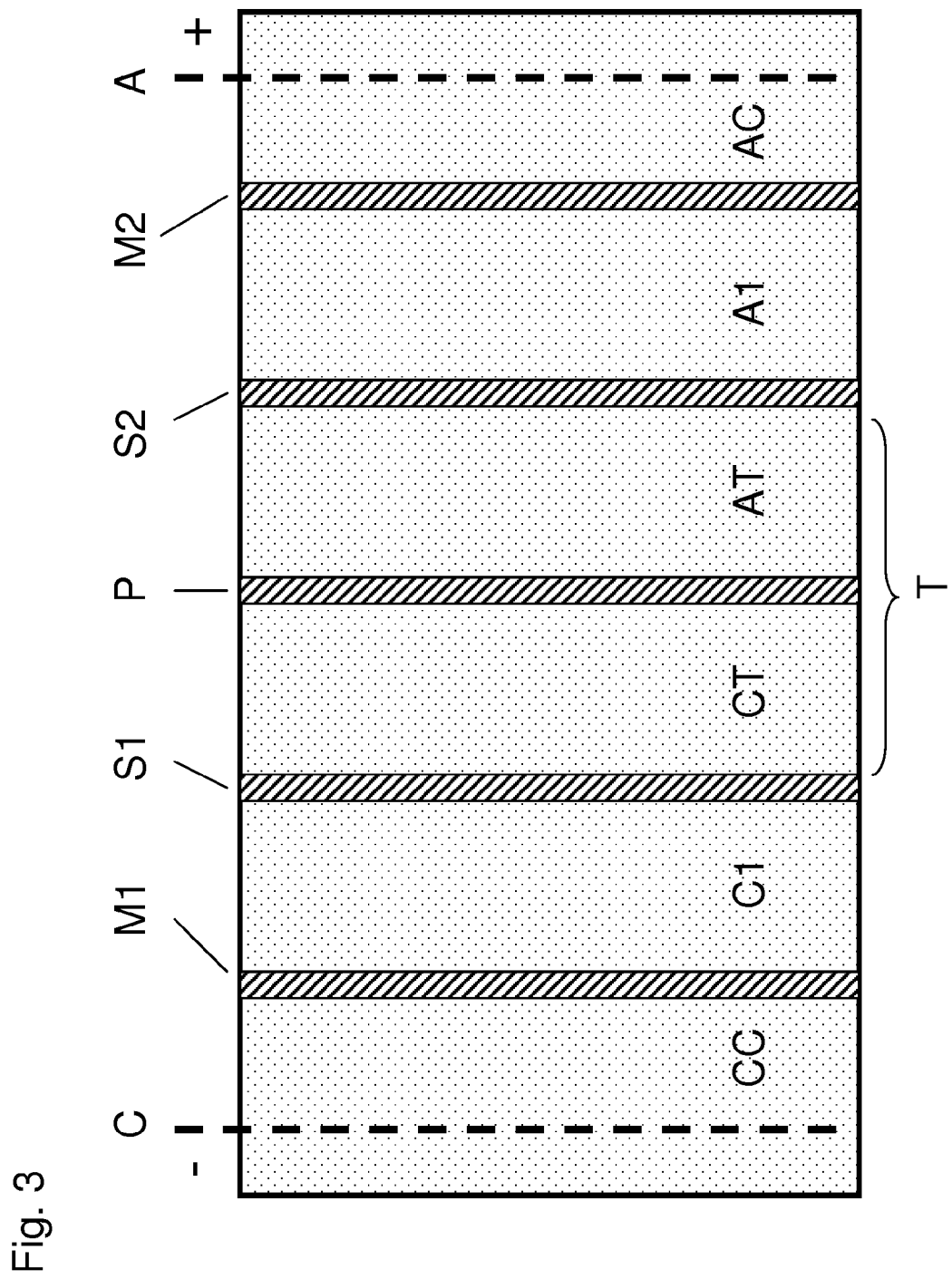

FIG. 3 schematically shows an electrochemical cell array for the treatment of samples via electro-(end-)osmotic flow with six compartments.

FIG. 1 shows an electrochemical cell for the treatment of samples such as biological material via electro-(end-)osmotic flow, with an electrode chamber, comprising a cathodic compartment (CC) and an anodic compartment (AC). A cathode (C) is arranged in the cathodic compartment (CC) and an anode (A), is arranged in the anodic compartment (AC). A treatment compartment (T) for the biological material is arranged between the cathodic compartment (CC) and the anodic compartment (AC). The treatment compartment (T) comprises a schematically illustrated holding device (P) for a solid sample such as biological material placed in said treatment compartment (T) and thereby dividing the treatment compartment into a cathodic treatment compartment (CT) and an anodic treatment compartment (AT). A first selective membrane (M1) is arranged between said cathodic compartment (CC) and said cathodic treatment compartment (CT). A second selective membrane (M2) is arranged between said anodic compartment (AC) and said anodic treatment compartment (A1). The selective membranes (M1, M2) are ion selective membranes. By placing e.g. a solid biological material such as pericardium in the holding device (P) and by applying electrical current, the chemical surroundings (pH, ionic strength, ion concentrations) in the compartments CC, CT, AT, and AC changes. Biological material might be negatively influenced.

FIG. 2 shows an electrochemical cell for the treatment of a sample such as biological material via electro-(end-) osmotic flow, comprising an electrode chamber with a cathodic compartment (CC) and an anodic compartment (AC). A cathode (C) is arranged in the cathodic compartment (CC) and an anode (A) is arranged in the anodic compartment (AC). The electrochemical cell further comprises an intermediate cathodic compartment (C1) and an intermediate anodic compartment (A1). Additionally, there is a first selective membrane (M1) which is arranged between said cathodic compartment (CC) and said first intermediate cathodic compartment (C1) and a second selective membrane (M2) being arranged between said anodic compartment (AC) and said first intermediate anodic compartment (A1).

The treatment compartment (T) for the sample or biological material is arranged between said intermediate cathodic compartment (C1) and said intermediate anodic compartment (A1). A first separator membrane (S1) is arranged between said treatment compartment (T) and said intermediate cathodic compartment (C1) and a second separator membrane (S2) arranged between said treatment compartment (T) and said intermediate anodic compartment (A1). A liquid or solid biological material is placed in the treatment compartment (T), an electric current is applied and despite a flow that is further illustrated with the examples the conditions within the treatment compartment (T) remain essentially constant.

FIG. 3 shows an electrochemical cell especially adapted for solid samples such as solid biological material. The basic structure is the same as in FIG. 2 so reference is made to FIG. 2. Elements with the same reference sign are identical to those of FIG. 2 so it is abstained to describe these elements again and the reader should refer to FIG. 2. The electrochemical cell of FIG. 3 additionally comprises a holding device (P) for solid biological material placed in said treatment compartment (T) dividing the treatment compartment into a cathodic treatment compartment (CT) and an anodic treatment compartment (AT). As mentioned above this embodiment is particularly suitable for the treatment of solid biological material since treatment is faster than in the above mentioned electrochemical cell with only five compartments. In this embodiment the cathodic treatment compartment (CT) is adjacent to the first separator membrane (S1) and the anodic treatment compartment (AT) is adjacent to the second separator membrane (S2). The holding device (P) is placed between cathodic treatment compartment (CT) and anodic treatment compartment (AT) so migration within the electrochemical cell has to occur through biological material placed in the holding device (P).

Now referring to both FIG. 2 and FIG. 3 the intermediate cathodic compartment (C1) and the intermediate anodic compartment (A1) are separated from the cathodic compartment (CC) and the anodic compartment (AC) through selective membranes (M1, M2) which are semi-permeable membranes. These selective membranes (M1, M2) prevent the mixing of the hydraulic fluids between the compartments, however, allow the passage of ions. Alternatively ion-exchange-membranes or -diaphragms can be used as selective membranes (M1, M2). Hence, the nature and amount of the ions entering the cathodic treatment compartment (CT) and the anodic treatment compartment (AT) can be controlled in accordance with the current flow. The choice of the as selective membranes (M1, M2) depends on the type of electrolyte used and the properties of the solution to be treated. A simultaneous use of an anion-exchange-membrane and a cation-exchange-membrane, or combinations thereof in position M1 or M2 ensure a defined supply and removal of ions into the cathodic treatment compartment (CT) and the anodic treatment compartment (AT).

The additional separator membranes (S1, S2) are electo-osmotically active. Solutes are transported through the biological barrier layer in the holding device (P) in FIG. 3 or the liquid biological material in FIG. 2 without any change at the desired concentrations of salt or pH.

EXAMPLES

Example 1 (Comparative Example)

Example 1 shows an electrochemical cell according to the prior art with four compartments and agarose gels as separating membranes (see FIG. 1). The electrochemical cell had a circular cross-section with a diameter of 2 cm and a membrane area of 3.14 cm$^2$.

As selective membranes M1 and M2 ion exchange membranes of the Nafiontyp were used. An electro-(end-)osmotically active separator membrane was place in holding device (P). This separator membrane consisted of cotton fabric coated with agarose gel. 1.5% by weight of agarose was dissolved in boiling water and applied to the cotton fabric still in liquid form. After solidification the separator membrane was placed position (P). All compartments (CC, CT, AT, AC) were filled with 50 mM phosphate buffer standard (3.4 g $KH_2PO_4$ and 4.3 g $K_2HPO_4$; dissolved in 500 ml water). When an electric voltage between the cathode (C) and anode (A) was applied, an electro-osmotic flow from anodic treatment compartment (AT) to cathodic treatment compartment (CT) took place. For comparison purposes, a cellulose film (Muscocell) was placed in position (P). When an electric voltage between the cathode (C) and anode (A) was applied, only a minimal electro-osmotic flow from anodic treatment compartment (AT) to cathodic treatment compartment (CT) took place. Cell currents, cell voltages, and the amounts of electrolyte removed from the cathodic treatment compartment (CT) that took place are shown in Table 1 below.

TABLE 1

Cell currents, cell voltages, and the amounts of electrolyte removed from the cathodic treatment compartment (CT)

| time (min) | electrolyte taken from compartment CT (g) | electric current (mA) | voltage (V) |
|---|---|---|---|
| Agarose-membrane | | | |
| 0 | — | — | — |
| 3 | — | 62.5 | 28.24 |
| 6 | 0.478 | 67.1 | 28.15 |
| 10 | — | 61.7 | 28.24 |
| Cellulose membrane | | | |
| 0 | 0.000 | 58.7 | 29.56 |
| 8 | 0.0302 | 73.7 | 29.19 |
| 30 | — | 68.9 | 29.45 |

After the experiments the electrolytes in the anodic treatment compartment (AT) and the cathodic treatment compartment (CT) were analyzed for their content of phosphate. The results are shown in Table 2.

TABLE 2

Phosphate concentrations in different compartments

| Sample solution | Phosphate [mM] |
|---|---|
| Agarose separator | |
| cathodic treatment compartment (CT) (10 min) | 23.0 |
| cathodic treatment compartment (CT) (10 min) | 23.3 |
| anodic treatment compartment (AT) (10 min) | 74.4 |
| anodic treatment compartment (AT) (10 min) | 75.8 |
| Cellulose separator | |
| cathodic treatment compartment (CT) (30 min) | 16.7 |
| cathodic treatment compartment (CT) (30 min) | 16.4 |
| anodic treatment compartment (AT) (30 min) | 105.0 |
| anodic treatment compartment (AT) (30 min) | 106.6 |
| Blank | 0.01 |
| 50 mM phosphate buffer | 70.7 |
| 50 mM phosphate buffer | 64.8 |

As can be seen from the experimental results by use of a suitable separator membrane (agarose membrane) an electro-osmotic fluid transport took place. A phosphate ion migration into anodic treatment compartment (AT) took place independently. Using the agarose—separator membrane the electro-osmotic flow from anodic treatment compartment (AT) to cathodic treatment compartment (CT) during the first 6 minutes was 0.025 ml/min cm$^2$ (the density of the electrolyte equals 1 g/ml). Due to concentration polarization and pH shift a decrease in the flow occurred. Although an ion transport was observed by using the unsuitable cellulose membrane as separator membrane (which can be determined by the change in the phosphate concentration), there was no substantial electro-osmotic flow. Hence, cellulose membranes under the present conditions are not suitable presumably due to the low number of carboxylic groups.

Example 2

Example 2 shows the proper use of five compartments in the electrochemical cell (FIG. 2) for the treatment of a liquid biological material, whereby the ion concentration is not adversely altered in biological liquid and the surroundings. A electrochemical cell with 5 chambers was used. The electrochemical cell had a circular cross-section with a diameter of 2 cm thus all membranes showed and active area of 3.14 cm$^2$.

As first and second selective membranes M1 and M2 ion exchange membranes of the Nafiontype were used. As electro-osmotically active separator membranes S1 and S2, cotton fabrics coated with agarose gel each were used that were prepared in accordance with example 1. After solidification, the separators were fixed in positions S1 and S2 in FIG. 2. All compartments (CC, C1, T, A1, AC) were filled with 50 mM phosphate buffer standard (see example 1). When an electric voltage between the cathode (C) and anode (A) was applied, an electro-osmotic flow from intermediate anodic compartment (A1) through treatment compartment (T) to intermediate cathodic compartment (C1) took place. Cell currents, cell voltages, and the amount of electrolyte removed from intermediate cathodic compartment (C1) are shown in Table 3.

TABLE 3

Cell currents, cell voltages, and the amount of electrolyte removed from intermediate cathodic compartment (C1)

| time (min) | electrolyte taken from compartment C1 (g) | electric current (mA) | voltage (V) |
|---|---|---|---|
| 0 | | — | — |
| 2 | | 58.6 | 30.4 |
| 10 | | 69.9 | 30.2 |
| 14 | 0.8272 | 70.6 | 30.3 |

After the experiments have been carried out, the electrolytes in intermediate cathodic compartment (C1), intermediate anodic compartment (A1), and treatment compartment (T) were investigated to determine the levels of phosphate. The results are shown in Table 4.

TABLE 4

Phosphate concentrations in different compartments

| Sample | solution phosphate mM |
|---|---|
| intermediate cathodic compartment (C1) (14 min) | 23.7 |
| intermediate cathodic compartment (C1) (14 min) | 23.4 |
| treatment compartment (T) (14 min) | 51.2 |
| treatment compartment (T) (14 min) | 51.6 |
| intermediate anodic compartment (A1) (14 min) | 78.2 |
| intermediate anodic compartment (A1) (14 min) | 77.4 |
| Blank | 0.43 |

As can be seen from the experimental results, the concentration of phosphate in cathodic treatment compartment (CT) virtually remained unchanged by the electro-osmotic flow. Electrolyte was transported into intermediate cathodic compartment (C1), while the negative phosphate ion of intermediate cathodic compartment (C1) migrated through treatment compartment (T) into intermediate anodic compartment (A1). The electro-osmotic flow from intermediate cathodic compartment (C1) to intermediate anodic compartment (A1) during the first 13 min was 0.019 ml/min cm$^2$ (the density of the electrolyte equals 1 g/ml).

Example 3

This example confirms the successful use of the present method for amino acids using the example of arginine. An electrochemical cell array with 5 compartments was used (FIG. 2). The electrochemical cell had a circular cross-section with a diameter of 2 cm and a membrane area of 3.14 cm$^2$ (see example 1).

As first and second selective membranes M1 and M2 ion-exchange-membranes of the Nafiontype were used. As electro-osmotically active separator membranes S1 and S2, cotton fabric coated with agarose gel as described in example 1 was used. After solidification, the separator membranes S1 and S2 were fixed in their positions. All compartments (CC, C1, T, A1, AC) were filled with 50 mM phosphate buffer standard (3.4 g KH$_2$PO$_4$ and 4.3 g of K$_2$HPO$_4$ dissolved in 500 ml water), which additionally contained 5 mM arginine hydrochloride.

After applying an electric voltage between the cathode (C) and anode (A), an electro-osmotic flow from intermediate anodic compartment (A1) to intermediate cathodic compartment (C1) via treatment compartment (T) took place. After an electrolysis time of 10 minutes an increased outflow of the electrolyte from treatment compartment (T) to intermediate cathodic compartment (C1) took place. Cell currents, cell voltages, and the removed amounts of electrolyte from intermediate cathodic compartment (C1) are shown in Table 5.

TABLE 5

Cell currents, cell voltages, and the amount of electrolyte removed from intermediate cathodic compartment (C1)

| time (min) | electrolyte taken from intermediate cathodic compartment (C1) (g) | electric current (mA) | voltage (V) |
|---|---|---|---|
| 0 | 0 | 41.8 | 30.45 |
| 10 | 0.635 | 54.8 | 30.33 |
| 15 | 0.913 | 53.1 | 30.30 |

A total amount of electrolyte of 0.913 g (density 1 g/ml) was transported to intermediate cathodic compartment (C1) only 0.16 g of which were added in treatment compartment (T). The vast majority (0.753 g, 82.5% by weight) was transported from intermediate anodic compartment (A1) through treatment compartment (T) into intermediate anodic compartment (A1). After the experiment the phosphate and arginine concentrations in the electrolyte in intermediate cathodic compartment (C1), treatment compartment (T) and intermediate anodic compartment (A1) were measured. The results are shown in Table 6.

TABLE 6

Phosphate and arginine concentrations in different compartments

| Sample solution | Phosphate [mM] | Arginine [mM] |
|---|---|---|
| intermediate cathodic compartment (C1) (15 min) | 27.6 | 3.01 |
| intermediate cathodic compartment (C1) (15 min) | 27.8 | |

TABLE 6-continued

Phosphate and arginine concentrations in different compartments

| Sample solution | Phosphate [mM] | Arginine [mM] |
|---|---|---|
| treatment compartment (T) (15 min) | 48.0 | 4.35 |
| treatment compartment (T) (15 min) | 53.5 | |
| intermediate anodic compartment (A1) (15 min) | 58.2 | 3.05 |
| intermediate anodic compartment (A1) (15 min) | 62.9 | |
| Standard 50 mM Phosphate/5 mM Arginine | 71.0 | 5.14 |
| Standard 50 mM Phosphate/5 mM Arginine | 59.6 | |
| Blank | | 0.95 |

As can be seen from the experimental results, the concentration of phosphate in treatment compartment (T) remained substantially unchanged. The arginine concentrations were changing in different ways. The highest concentrations were observed in treatment compartment (T), since an almost steady-state of supply and removal by the electro-osmotic flow was achieved. The decrease in arginine concentration compared to the initial concentration of 5 mM can also be explained by possible binding of arginine to acidic groups of the agarose gel, since agarose gel also has ion exchange properties. The negative phosphate ion migrated from intermediate cathodic compartment (C1) through treatment compartment (T) to intermediate anodic compartment (A1). The electro-osmotic flow from intermediate anodic compartment (A1) to intermediate cathodic compartment (C1) during the first 10 minutes was 0.020 ml/min cm$^2$ (density of the electrolyte of 1 g/ml).

Example 4

Example 4 confirmed that fixed pericardium is also a suitable material for performing electro-(end-)osmotic treatment. An electrochemical cell with 5 compartments (FIG. 2) was used. The electrochemical cell has a circular cross-section with a diameter of 2 cm and a membrane area of 3.14 cm$^2$ (see above examples).

As selective membranes M1 and M2 ion exchange membranes of the Nafiontype were used. As electro-osmotically active separator membranes S1 and S2 glutaraldehyde fixed calf pericardium was used. The separator membranes S1 and S2 were stored in 0.25% by weight aqueous glutaraldehyde solution. Before assembling them into the electrochemical cell the separator membranes S1 and S2 were rinsed for 2×5 minutes each with 50 mM phosphate buffer to remove free glutaraldehyde. All compartments (CC, C1, T, A1, AC) were filled with 50 mM phosphate buffer standard (3.4 g KH$_2$PO$_4$ and 4.3 g of K$_2$HPO$_4$ dissolved in 500 ml water) additionally containing 5 mM arginine hydrochloride. After applying an electric voltage between the cathode (C) and anode (A), an electro-osmotic flow from intermediate anodic compartment (A1) to intermediate cathodic compartment (C1) took place via treatment compartment (T). Cell currents, cell voltages, and the removed amounts of electrolyte from intermediate cathodic compartment (C1) are shown in Table 7.

TABLE 7

Cell currents, cell voltages, and the removed amounts of electrolyte from intermediate cathodic compartment (C1)

| time (min) | electrolyte taken from intermediate cathodic compartment (C1) (g) | electric current (mA) | voltage (V) |
|---|---|---|---|
| 0 | | 60 | 30.29 |
| 3 | | 61.1 | 30.22 |
| 5 | 0.832 | 65.9 | 30.21 |

After the experiments, the phosphate and glutardialdehyde concentrations in the electrolyte were measured in intermediate cathodic compartment (C1), treatment compartment (T) and intermediate anodic compartment (A1). The results are shown in Table 8.

TABLE 8

Phosphate and glutardialdehyde concentrations in different compartments

| Sample solution | Phosphate [mM] |
|---|---|
| intermediate cathodic compartment (C1) (5 min) | 30.5 |
| treatment compartment (T) (5 min) | 48.2 |
| intermediate anodic compartment (A1) (5 min) | 51.3 |
| 50 mM phosphate Standard | 47.7 |

As can be seen from the experimental results, the concentration of phosphate in treatment compartment (T) remained substantially constant. The concentrations of free glutardialdehyde retained in all the compartments remained below the detection limit. Electrolyte is transported through the pericardium into intermediate cathodic compartment (C1), while the negatively charged phosphate ion migrates from intermediate cathodic compartment (C1) to intermediate anodic compartment (A1) via treatment compartment (T). The electro-osmotic flow from intermediate anodic compartment (A1) to intermediate cathodic compartment (C1) during the first 5 min was 0.053 ml/min cm$^2$ (density of the electrolyte of 1 g/ml).

If the experiment was continued, concentration polarization due to migration of the phosphate ions from compartment 2 to compartment 3 lead to changes in the electro-osmotic flow because of shifts in the pH. By reversing the polarity of the electrochemical cell a reversal of the ion migration and electro-osmotic flow occurred. After a 7 mM continuous electrolysis with reversed polarity the following phosphate concentrations were determined in the compartments (Table 9).

TABLE 9

(reversed polarity): Phosphate concentrations in different compartments

| Sample solution | Phosphate [mM] |
|---|---|
| intermediate cathodic compartment (C1) (7 min) | 58.3 |
| treatment compartment (T) (7 min) | 51.0 |
| intermediate anodic compartment (A1) (7 min) | 40.7 |
| 50 mM phosphate Standard | 47.7 |

Example 5

Example 5 confirmed the separation of a non-charged molecule from a solution to be treated, wherein the ion content in the solution remained unchanged. An electrochemical cell array with 5 compartments (FIG. 2) was used.

The electrochemical cell had a circular cross-section with a diameter of 2 cm and a membrane area of 3.14 cm$^2$ (see above examples).

As selective membranes M1 and M2 ion exchange membranes of the Nafiontype were used. As electro-osmotically active separator membranes S1 and S2, cotton fabric coated with agarose gel as described in example 1 were used. After solidification, the separator membranes S1 and S2 were fixed in their positions. All compartments (CC, C1, T, A1, AC) were filled with 50 mM phosphate buffer standard (3.4 g KH$_2$PO$_4$ and 4.3 g of K$_2$HPO$_4$ dissolved in 500 ml water). The buffer solution in treatment compartment (T) additionally contained 1 g/l glucose monohydrate.

After applying an electric voltage between the cathode (C) and anode (A), an electro-osmotic flow from intermediate anodic compartment (A1) to intermediate cathodic compartment (C1) took place via treatment compartment (T). After 13 min of electrolysis minutes an increased outflow of the electrolyte from treatment compartment (T) to intermediate cathodic compartment (C1) took place due the increased flow of electrolyte from treatment compartment (T) to intermediate cathodic compartment (C1). At this time, the electrolyte in intermediate cathodic compartment (C1) was re-filled with 50 mM phosphate solution. Cell currents, cell voltages, and the removed amounts of electrolyte from the intermediate cathodic compartment (C1) are shown in Table 10.

TABLE 10

Cell currents, cell voltages, and the removed amounts of electrolyte from the intermediate cathodic compartment (C1)

| time (min) | electrolyte taken from intermediate cathodic compartment (C1) (g) | electric current (mA) | voltage (V) |
|---|---|---|---|
| 0 | 0 | 62.8 | 30.28 |
| 13 | 0.6574 | 68.4 | 30.23 |
| 16 | 0 | 79.4 | 30.05 |
| 32 | 0.6037 | 83.7 | 30 |

After the experiment, the phosphate and glucose concentrations in the electrolyte intermediate cathodic compartment (C1), treatment compartment (T), and intermediate anodic compartment (A1) were examined. The results are shown in Table 11.

TABLE 11

Phosphate and glucose concentration in different compartments

| Sample solution | Phosphate [mM] | Glucose [g/l] |
|---|---|---|
| intermediate cathodic compartment (C1)/1 (13 min) | 21.9 | 0.15 |
| treatment compartment (T) (32 min) | 58.8 | 0.65 |
| intermediate anodic compartment (A1) (32 min) | 96.5 | 0.05 |
| intermediate cathodic compartment (C1)/2 (32 min) | 25.2 | 0.11 |
| Standard 50 mM phosphate | 49.1 | |
| Standard 50 mM phosphate/glucose | 54.7 | |
| Blank | | 0.03 |
| Standard 0.5 g/l | | 0.50 |
| Standard 1 g/l | | 1.10 |

As can be seen from the experimental results, the concentration of phosphate in treatment compartment (T) remained substantially constant, while glucose concentration decreased in treatment compartment (T) and increased in intermediate cathodic compartment (C1). By the electro-osmotic flow glucose was transported into intermediate cathodic compartment (C1), while the negative phosphate ion migrated from intermediate cathodic compartment (C1) through treatment compartment (T) into intermediate anodic compartment (A1). The electro-osmotic flow from intermediate anodic compartment (A1) to intermediate cathodic compartment (C1) was 0.016 ml/min cm$^2$ (density of the electrolyte of 1 g/ml) during the first 13 min.

Example 6

Example 6 confirmed the separation of a non-charged molecule from a solution to be treated, wherein the ion content in the solution remains unchanged. An electrochemical cell array with 5 compartments was used (FIG. 2). The electrochemical cell had a circular cross-section with a diameter of 2 cm and a membrane area of 3.14 cm$^2$ (see examples above).

As selective membranes M1 and M2 ion exchange membranes of the Nafiontype were used. As electro-osmotically active separator membranes S1 and S2, cotton fabric coated with agarose gel as described under example 1 was used. After solidification, the separator membranes S1 and S2 were fixed in their positions. All compartments (CC, C1, T, A1, AC) were filled with 50 mM phosphate buffer standard (3.4 g KH$_2$PO$_4$ and 4.3 g of K$_2$HPO$_4$ dissolved in 500 ml water). The buffer solution in treatment compartment (T) additionally contained 1 g/l glucose monohydrate.

After applying an electric voltage between the cathode (C) and anode (A), an electro-osmotic flow from intermediate anodic compartment (A1) to intermediate cathodic compartment (C1) took place via compartment 5. After electrolysis time of 13 minutes an increased outflow of the electrolyte from compartment 5 to compartment 2 took place due the increased flow of electrolyte from treatment compartment (T) to intermediate cathodic compartment (C1). At this time, the electrolyte in intermediate cathodic compartment (C1) was re-filled with 50 mM phosphate solution. Cell currents, cell voltages, and the removed amounts of electrolyte from the intermediate cathodic compartment (C1) are shown in Table 12.

TABLE 12 currents, cell voltages, and the removed amounts of electrolyte from the intermediate cathodic compartment (C1)

| time (min) | electrolyte taken from intermediate cathodic compartment (C1) (g) | electric current (mA) | voltage (V) |
|---|---|---|---|
| 0 | 0 | 60.5 | 30.38 |
| 8 | 0.7595 | 69.1 | 30.12 |
| 16* | 0 | 76.8 | 29.95 |
| 22 | 0.6047 | 77.0 | 29.9 |

*0.25 ml phosphate buffer refilled in compartment 5 after a total flow of 1.364 ml (density of electrolyte of 1 g/ml).

After the experiment, the phosphate and glucose concentrations in the electrolyte in intermediate cathodic compartment (C1), treatment compartment (T) and intermediate anodic compartment (A1) were examined. The results are shown in Table 13.

TABLE 13

Phosphate and glucose concentration in different compartments

| Sample solution | Phosphate [mM] | Glucose [g/l] |
|---|---|---|
| intermediate cathodic compartment (C1)/1 (8 min) | 31.5 | 0.19 |
| treatment compartment (T) (22 min) | 53.2 | 0.68 |
| intermediate anodic compartment (A1) (22 min) | 89.6 | 0.10 |
| intermediate cathodic compartment (C1)/2 (22 min) | 27.7 | 0.17 |
| Standard 50 mM phosphate | 47.7 | |
| Standard 50 mM phosphate/glucose | 46.5 | |
| Blank | | 0.07 |
| Standard 1 g/l | | 1.09 |

As can be seen from the experimental results, the concentration of phosphate in treatment compartment (T) remained substantially unchanged, while the glucose concentration decreased in treatment compartment (T) and decreased in intermediate cathodic compartment (C1). By the electro-osmotic flow glucose was transported into intermediate cathodic compartment (C1), while the negative phosphate ion migrated from intermediate cathodic compartment (C1) through treatment compartment (T) into intermediate anodic compartment (A1). The electro-osmotic flow from intermediate anodic compartment (A1) to intermediate cathodic compartment (C1) during the first 8 minutes was 0.030 ml/min cm$^2$.

Example 7

Example 7 shows the possibility for the treatment of solid porous samples by using fixed glutaraldehyde pericardium in the holding device (P). An electrochemical cell with six compartments was used (FIG. 3). The electrochemical cell had a circular cross-section with a diameter of 2 cm and a membrane area of 3.14 cm$^2$ (see above examples).

As selective membranes M1 and M2 ion exchange membranes of the Nafion-type were used. As electro-osmotically active separator membranes S1 and S2 glutaraldehyde fixed calf pericardium was used as described above. The pericardium to be treated was placed in the holding device (P). All compartments (CC, C1, CT, AT, A1, AC) were filled with 50 mM phosphate buffer standard (3.4 g KH$_2$PO$_4$ and 4.3 g of K$_2$HPO$_4$ dissolved in 500 ml water), which additionally contained 5 mM arginine hydrochloride. All pericardia were stored in 0.25% by weight aqueous glutaraldehyde solution. Before assembling them into the electrochemical cell the separator membranes S1 and S2 and the pericardium to be treated were rinsed for 2×5 minutes each with 50 mM phosphate buffer to remove free glutaraldehyde.

After applying an electric voltage between the cathode (C) and anode (A), an electro-osmotic flow from intermediate anodic compartment (A1) to anodic treatment compartment (AT), the pericardium to be treated in Position (P) and from cathodic treatment compartment (CT) to intermediate cathodic compartment (C1) took place. Cell currents, cell voltages, and the removed amounts of electrolyte from the cathodic treatment compartment (CT) are shown in Table 14.

TABLE 14

Cell currents, cell voltages, and the removed amounts of electrolyte from the cathodic treatment compartment (CT)

| time (min) | electrolyte taken from cathodic treatment compartment (CT) (g) | electric current (mA) | voltage (V) |
|---|---|---|---|
| 0 | | 47.6 | 30 |
| 5 | | 51.1 | 30 |
| 10 | 0.9187 | 52.0 | 30 |

After the experiment, the electrolyte in intermediate cathodic compartment (C1), cathodic treatment compartment (CT), anodic treatment compartment (AT), and intermediate anodic compartment (A1) were analysed with respect to phosphate concentrations. The results are shown in Table 15.

TABLE 15

Phosphate concentration in different compartments

| Sample solution | Phosphate [mM] |
|---|---|
| intermediate cathodic compartment (C1) (10 min) | 33.6 |
| cathodic treatment compartment (CT) (10 min) | 45.6 |
| anodic treatment compartment (A1) (10 min) | 46.0 |
| intermediate anodic compartment (A1) (10 min) | 61.5 |
| Standard 50 mM phosphate | 46.5 |

As can be seen from the experimental results, the concentrations of phosphate in the cathodic treatment compartment (CT) and anodic treatment compartment (AT) were practically unchanged by the arrangement according to the invention. Electrolyte was transported from anodic treatment compartment (AT) to cathodic treatment compartment (CT) through position (P) carrying the pericardium. The negative phosphate ion migrates from intermediate cathodic compartment (C1) through cathodic treatment compartment (CT) and anodic treatment compartment (AT) into intermediate anodic compartment (A1). The electro-osmotic flow from anodic treatment compartment (AT) to cathodic treatment compartment (CT) during the first 10 minutes is 0.029 ml/min cm$^2$ (density of the electrolyte of 1 g/ml).

The experiment was repeated for confirmation. For this purpose, the electrochemical cell was completely emptied and filled with fresh 50 mM phosphate buffer solution. Cell currents, cell voltages, and the removed amounts of electrolyte from the cathodic treatment compartment (CT) are shown in Table 16.

TABLE 16

Cell currents, cell voltages, and the removed amounts of electrolyte from the cathodic treatment compartment (CT)

| time (min) | electrolyte taken from cathodic treatment compartment (CT) (g) | electric current (mA) | voltage (V) |
|---|---|---|---|
| 0 | | 51.7 | 30 |
| 5 | | 50.0 | 30 |
| 9 | | 50.4 | 30 |
| 10 | 0.8613 | — | — |

After the experiment, the electrolyte in intermediate cathodic compartment (C1), cathodic treatment compartment (CT), anodic treatment compartment (AT), and intermediate anodic compartment (A1) was analysed with respect to phosphate concentration. The results are shown in Table 17.

TABLE 17

Phosphate concentration in different compartments

| Sample solution | Phosphate [mM] |
|---|---|
| intermediate cathodic compartment (C1) (10 min) | 34.1 |
| cathodic treatment compartment (CT) (10 min) | 46.0 |
| anodic treatment compartment (AT) (10 min) | 44.3 |
| intermediate anodic compartment (A1) (10 min) | 66.5 |
| Standard 50 mM phosphate | 46.5 |

As can be seen from the experimental results, the concentration of phosphate in cathodic treatment compartment (CT) and anodic treatment compartment (AT) was practically unchanged by the arrangement according to the invention. Due to the electro-osmotic flow electrolyte was transported through pericardium in position (P) from anodic treatment compartment (AT) to cathodic treatment compartment (CT). The negative phosphate of intermediate cathodic compartment (C1) migrates through cathodic treatment compartment (CT) and anodic treatment compartment (AT) into intermediate anodic compartment (A1). The electro-osmotic flow from anodic treatment compartment (AT) to cathodic treatment compartment (CT) during the first 10 minutes was 0.027 ml/min cm$^2$ (density of the electrolyte of 1 g/ml). By reversing polarity of the electrochemical cell array, the direction of the flow reversed.

The invention claimed is:

1. An electrochemical cell for the treatment of a sample via electro-(end-)osmotic flow, comprising:
   (i) an electrode chamber,
   (ii) a cathode, being arranged in a cathodic compartment of said electrode chamber,
   (iii) an anode, being arranged in an anodic compartment of said electrode chamber,
   (iv) an intermediate cathodic compartment,
   (v) an intermediate anodic compartment,
   (vi) a first selective membrane being arranged between said cathodic compartment and said first intermediate cathodic compartment,
   (vii) a second selective membrane being arranged between said anodic compartment and said first intermediate anodic compartment, and
   (viii) a treatment compartment for the sample being arranged between said intermediate cathodic compartment and said intermediate anodic compartment, further comprising a first separator membrane between said treatment compartment and said intermediate cathodic compartment and a second separator membrane arranged between said treatment compartment and said intermediate anodic compartment,
   wherein the first separator membrane and the second separator membrane are electro-(end-)osmotically active membranes, and
   wherein the first separator membrane and the second separator membrane comprise a gel.

2. The electrochemical cell according to claim 1, wherein the sample is a solid sample, and wherein the electrochemical cell further comprises:
   (ix) a holding device for the solid sample placed in said treatment compartment dividing the treatment compartment into a cathodic treatment compartment and an anodic treatment compartment,
   wherein the holding device is configured so that when it carries the solid sample and is placed in the treatment compartment said holding device divides the treatment compartment into two separated compartments, the cathodic treatment compartment and the anodic treatment compartment, with the solid sample being exposed to both the cathodic treatment compartment and the anodic treatment compartment, wherein the holding device is placed between the cathodic treatment compartment and the anodic treatment compartment so that migration within the electrochemical cell occurs through biological material placed in the holding device.

3. The electrochemical cell according to claim 1, wherein the first separator membrane and the second separator membrane are composed of identical material.

4. The electrochemical cell according to claim 1, wherein the first selective membrane and the second selective membrane are selected from the group consisting of semipermeable membranes, ion exchanger membranes, ion-exchange diaphragms, and combinations thereof.

5. A method of treating a sample via electro-(end-)osmotic flow using an electrochemical cell according to claim 1, comprising placing an electrolyte in each of the cathodic compartment, the intermediate cathodic compartment, the intermediate anodic compartment, the anodic compartment, and the treatment compartment, placing the sample in the treatment compartment, and applying an electric current to the cathode and anode.

6. A method for treating a solid sample via electro-(end-)osmotic flow using an electrochemical cell according to claim 2, comprising placing an electrolyte in each of the cathodic compartment, the intermediate cathodic compartment, the intermediate anodic compartment, the anodic compartment, the cathodic treatment compartment, and the anodic treatment compartment, placing a solid sample in the holding device which is placed in the treatment compartment, and applying an electric current to the cathode and anode.

7. The method according to claim 5, wherein the sample comprises a solid biological material.

8. The method according to claim 7, wherein the solid biological material comprises pericardium.

9. The method according to claim 5, wherein the sample comprises a liquid biological material.

10. The method according to claim 9, wherein the liquid biological material is selected from the group consisting of blood and plasma.

11. The electrochemical cell according to claim 1, wherein the gel is selected from the group consisting of agarose gel, pectin gel, and swollen cellulose.

12. The method according to claim 5, wherein the sample comprises a biological material.

13. The method according to claim 6, wherein the solid sample comprises a solid biological material.

* * * * *

UNITED STATES PATENT AND TRADEMARK OFFICE
CERTIFICATE OF CORRECTION

PATENT NO. : 10,369,522 B2
APPLICATION NO. : 15/107663
DATED : August 6, 2019
INVENTOR(S) : Kofler et al.

It is certified that error appears in the above-identified patent and that said Letters Patent is hereby corrected as shown below:

In the Specification

Column 2
Line 13, change "charge" to –charges–

Column 3
Line 28, change "an" to –a–

Column 7
Line 30, change "however, allow" to –however, they allow–

Column 9
Line 14, change "and" to –an–

Column 13
Line 18, delete "minutes"
Line 20, change "due the" to –due to the–

Column 14
Line 37, change "due the" to –due to the–

In the Claims

Column 18
Line 28, change "compartment" to –compartments–
Line 36, change "compartment" to –compartments–

Signed and Sealed this
Third Day of March, 2020

Andrei Iancu
*Director of the United States Patent and Trademark Office*